(12) United States Patent
Bader (10) Patent No.: US 6,379,956 B1
(45) Date of Patent: Apr. 30, 2002

(54) METHOD FOR POPULATING SUBSTRATES WITH BIOLOGICAL CELLS AND POPULATING DEVICES THAT CAN BE USED THEREFOR

(76) Inventor: Augustinus Bader, Hinter den langen Hofen 16, 31275 Immensen (DE)

( * ) Notice: Subject to any disclaimer, the term of this patent is extended or adjusted under 35 U.S.C. 154(b) by 0 days.

(21) Appl. No.: 09/719,040

(22) PCT Filed: Apr. 7, 2000

(86) PCT No.: PCT/DE00/01047

§ 371 Date: Feb. 21, 2001

§ 102(e) Date: Feb. 21, 2001

(87) PCT Pub. No.: WO00/59618

PCT Pub. Date: Oct. 12, 2000

(30) Foreign Application Priority Data

Apr. 7, 1999 (DE) .......................................... 199 15 610

(51) Int. Cl.[7] ................................................. C12N 5/00
(52) U.S. Cl. ...................... 435/325; 435/42; 435/173.1; 435/173.2; 435/173.4; 435/173.5; 435/173.6; 435/174; 435/176; 435/177; 435/180; 435/240.1; 435/383.1; 435/383.2
(58) Field of Search ............................... 435/42, 173.1, 435/173.2, 173.4, 173.5, 173.6, 174, 176, 177, 180, 240.1, 325, 383.1, 385.2

(56) References Cited

U.S. PATENT DOCUMENTS

| | | |
|---|---|---|
| 5,035,708 A | 7/1991 | Alchas et al. |
| 5,155,035 A | 10/1992 | Schwarz et al. |
| 5,492,826 A | 2/1996 | Townsend et al. |
| 6,010,573 A | 1/2000 | Bowlin |

FOREIGN PATENT DOCUMENTS

| | | | |
|---|---|---|---|
| DE | 195 46 542 C1 | | 5/1997 |
| DE | 197 25 318 A1 | | 12/1998 |
| EP | 0 320 441 A1 | | 12/1987 |
| EP | 0 704 244 A2 | | 4/1996 |
| GB | 2002814 A | * | 2/1979 |
| GB | 2 002 814 A | | 2/1979 |
| WO | WO 92/22634 | | 12/1992 |
| WO | WO 93/01843 | | 2/1993 |
| WO | WO 95/07344 | | 3/1995 |
| WO | WO 97/49799 | | 12/1997 |
| WO | WO 98/32367 | | 7/1998 |

OTHER PUBLICATIONS

Gosselin et al.ePTFE Coating with Fibrin Glue, FGF–1, and Heparin: Effect on retention of Deeded Endothelial Cells. 1996. J. Surgical Rexearch, 60:327–332.*
Maniatis et al. Molecular cloning—A Laboratory Manual, Cold Spring Harbor Laboratory, 1982, p. 60, Lines 12–13.*
Srivastava, K.C., Biodegradation of styrene by thermophillic Bacillus isolates. 1990. In "Opportunities in Biotransformations", Copping et al. (editors), Elsevier Applied Science, pp. 53–58.*
Singleton et al., 1993. Dictionary of Microbiology and Molecular Biology. John Wiley and Sons., p. 827.*
W.W. Minuth, S. Kloth, J. Aigner, M. Sittinger & W. Röckl, "Organo–typical environment for cultured cells and tissues", *BIOforum*, 17 (1994), pp. 412–416.

* cited by examiner

Primary Examiner—Francisco Prats
Assistant Examiner—Kailash C. Srivastava
(74) Attorney, Agent, or Firm—Whitham, Curtis & Christofferson (57) ABSTRACT

The populating method for populating a substrate with living cells provides a population with at least one populating phase and at least one perfusion phase. During the populating phase the substrate can be held in contact with the cell suspension by continuous rotation in various spatial arrangements. The populating device of the invention (10) comprises a rollable container (10*a*) and a removable insert in it with a means (12) for inserting the substrate being populated, such as a plastic or collagen matrix. The insert is designed so that in interaction with the inserted substrate, two liquid-tight chambers are formed within the container on opposite sides of the inserted substrate, so as to allow separate populating of both sides of the substrate. The container have liquid inlets and outlets (16) and may also have gas inlets and outlets. The rollable populating reactor (10) is inserted into a roller cabinet for certain phases of the populating.

30 Claims, 7 Drawing Sheets

METHOD FOR POPULATING SUBSTRATES WITH BIOLOGICAL CELLS AND POPULATING DEVICES THAT CAN BE USED THEREFOR

BACKGROUND OF THE INVENTION

1. Field of the Invention

The invention concerns a method for populating substrates with living biological cells and populating devices that can be used therefor.

2. Background Description

For various purposes, it is desired to populate substrates or matrices with cells which should then grow on those substrates. Both substrates of natural origin and those of synthetic origin are considered. Examples of substrates of natural origin might, for instance, be collagen substrates. Synthetic substrates could, for instance, be biologically inert plastics. The substrates to be populated with living cells often have a net-like or sponge-like structure to make it easier for the cells to grow into them.

For populating, the cells must be taken to the substrate without being damaged or destroyed; and they must be applied to the substrate in such a manner that growth can occur. In most cases, one tries for a closed cell lawn.

The cultured cells, or cells removed elsewhere, are generally in a culture medium. In the usual inoculation processes, usually done on the laboratory scale, the substrate is brought into contact with the cells in the culture medium, for instance, in a "roll flask". The roll flask is rolled in a rolling incubator, so that the substrate, the culture medium, and the cells are maintained in constant but not overly vigorous motion.

With inoculation there is the problem that the substrate must be flushed by the culture medium with the cells, because cells should be transported continuously to the surface, but on the other hand, the flow, or the rolling or pivoting motion within the flask must not be so great that the freshly applied cells are swept off again before they can successfully become established. There is also the problem that the substrate should be accessible to the cells at all points. Therefore it must not fold because of the rolling motion, or stick to the roll flask.

In previous inoculation experiments, there was little or no ability to attain normal differentiation of the growing cells. The artificially inoculated substrates are therefore distinct from the natural precursors in the structure of their cell layers.

Another disadvantage of previous inoculation methods was that complete confluence of the endothelial cell lawn could not be developed in bioartificial vessels.

It would be desirable, then, for a process to be developed in which the cells used for inoculation were enabled by the culture conditions to develop cell colonies typical of the tissue, and to develop physiological differentiation.

SUMMARY OF THE INVENTION

The invention is, therefore, based on the objective of developing an inoculation method and inoculating means usable for it, with which a substrate can be inoculated under optimal growth conditions. The inoculating means to be developed should provide effective inoculation without expensive apparatus. Furthermore, handling of the substrate should be reliable and simple during the entire inoculation process.

The inoculating means should preferably be usable simultaneously as a vessel for sterilization, acellularization [see Note 2], storage, transportation, and frozen preservation. That is desired to avoid breaking the chain of sterility up to the end user.

This objective is attained by a process for inoculating substrates with biological cells in which the substrate held within a device and the cells provided for inoculation are subjected to at least one inoculation phase, during which the substrate is rotated about at least one axis in or with the device and the cells are repeatedly brought into contact with the substrate during the rotary movement, and in which the substrate is subjected to at least one perfusion phase during or after one or more inoculation phases, during which the substrate is perfused in at least regions of its external or internal surface.

By inoculation phase we mean, with respect to this invention, a phase in cells with which the substrate is to be inoculated are taken to the substrate in a suitable manner. Preferably, during the inoculation phase, cells are moved to the substrate in a medium or by streaking on the substrate, insertion into the substrate, or coating of the substrate with a medium containing the cells (e. g., collagen). In this process the cells can be provided with factors or cofactor, especially growth factors or chemotactic factors.

By perfusion phase we mean, with respect to this invention, a phase during which the substrate is perfused, as in the usual expert terminological use of the concept "perfusion". Preferably, the substrate is perfused with a liquid nutrient medium for cell culture, blood, or plasma, which can in turn be enriched with various substances.

Multiple inoculation and perfusion phases can take turns with each other during the process, preferably alternately. While carrying out the inoculation phase in a similar manner was already known, it was found, surprisingly, that incorporation of one or more perfusion phases in the process distinctly improves the result of the inoculation. Use of the perfusion phases simulates quasiphysiological conditions which are important for development of normal cell differentiation. Shear stress produced to the extent intended by the perfusion, differentiates endothelial cells. Smooth muscle cells react to pulsatile pressures, which can also be generated during the perfusion. Oxygen and nutrients can be provided during the perfusion, and pressure stresses can be applied. Physiological pressure fluctuations, such as occur in vivo between systole and diastole are particularly important for orientation of the newly formed cells (of the extracellular matrix) and development of normal stability and ability to bear pressure stress. Inoculation of a synthetic tubular vessel on its interior has already been described in Br. J. Surg. 1991, Vol. 78, 878–882. The inoculation is done with aliquots of an endothelial cell suspension while the vessel is rotated. In that work it was determined that the inoculation of the PTFE [poly(tetrafluoroethylene); Teflon] vessel coated with fibronectin could be significantly improved in its ability to withstand pulsing flowing blood if, instead of a short (20-minute) inoculation cycle, a longer cycle was used overnight in a rolling incubator. However, it was not recognized there that intentional perfusion of the inoculated vessel can itself improve the result of inoculation. Furthermore, the device described there can be rotated only about its own axis and not in many spatial directions. Also, mounting and dismounting of the vessel are intricate, as caps must be removed from both ends. In removal of the finished inoculated vessel there is a danger that the structure will become unsterile because several intricate manipulations are required to remove the vessel from the reactor.

It is preferable for the rotation of the substrate during the inoculation phase to be done in a superimposed rotary motion about at least two spatial axes. This can also be a randomly controlled rotation in all spatial directions, which will be considered further in relation to suitable inoculating devices for the process. Alternatively, the rotation of the substrate during the inoculation phases can be about at least two spatial axes successively or alternately.

The process can also be set up so that the substrate is subjected to a supplementary resting phase after at least one inoculation phase. Such a resting phase can be inserted to provide the partially or completely inoculated substrate a stress-free consolidation phase during which the cell lawn can strengthen itself or even reorganize internally.

The intermittent perfusion also allows development of multilayer structures. That can be done, for instance, in multiple inoculation phases, adding first connective tissue cells, smooth muscle cells, and then endothelial cells, with perfusion phases between the individual inoculation phases. Thus the following cell types can be applied to already structured associations differentiated typically for the tissue.

Inoculation with fibroblasts/smooth muscle cells can be conducted for days and weeks until finally the endothelial lawns are cultured within a few hours to days. The endothelial cells can be preserved advantageously in deep cold in the meantime, so that they do not experience unnecessary culture duration. In addition, new matrix-forming cells can be added repeatedly. A repeated application of cells alternating with perfusion phases is possible. That means changing from rotational movements of the inoculation device to perfusions at rest. For that, the inoculating device can remain stationary in vertical, horizontal, or any other position. This is important for producing heart valves. A pulsing operation to be described in more detail below is preferably done in a vertical position of the heart valve. Thus spontaneous closure of the valve seal due to gravity is possible after completion of the pulsation phase.

Furthermore, the process can comprise other phases with additional process steps for handling of the already populated, partially populated, or not yet populated substrate. For instance, preliminary acellularization of the substrate to be inoculated, one or more flushing phases, sterlzation, and/or different gassings can be included in the overall process without need to open the bioreactor and move the substrate.

In further development of the invention, growth factors or cells embedded in auxiliary substances such as hydrogels can be added. Especially for inoculation of a tube, a collagen matrix, for instance (Type I or mixtures with other matrix components) or a fibrinogen or fibronectin mixture with cells can be added externally and/or internally to a tube. That can be done by streaking or dropping. For instance, VEGF or PDGF can be applied as growth factors and chemotactic factors specific for cell types. In this way, gradients for migration of connective tissue cells can be developed. To the extent that different cell types can be cultivated in the different chambers, the medium can be adapted to the corresponding cell types.

Interruptions with or without previous or subsequent cryopreservative steps can be carried out for the sterilization or storage phases. The perfusion can preferably be carried out with pulsation. This process serves to provide more natural simulation of physiological conditions. As previously mentioned, smooth muscle cells in particular react to pulsatile pressures, so that such a further developed process can be offered, for example, for inoculating with smooth muscle cells. The inoculating device described later in more detail is particular suitable for this, as the substrate can be moved to the interior by altering the position of the device in various settings. The substrate is also provided with enough space for flexible volume changes (to larger or smaller volumes).

Finally, the substrate can be inoculated with different cells in particular areas by the process of the invention, to the extent desired for the particular substrate. That is particularly possible, as described in more detail below, with the inoculating device specially developed for this process, with which multiple chambers or compartments separate from each other are formed, bordering on the substrate, which is exposed to different media or inoculation culture solutions, and can also be perfused separately. Alternately, it is also possible to protect regions of the substrate, i.e., to cover it or block it off, and then to treat various regions successively in different steps.

If desired, the substrate can also be inoculated successively with different cells, so that multiple layers with different cells can be formed on the substrate.

The substrate used, which is preferably flat or tubular as described in the preceding or following, can itself have internal chambers or can be double-waled or multiwalled. It can also be porous or spongy, so that the cells can settle in the pores or channels of this material.

The substrate can comprise a biological material of natural origin (xenogenic, allogenic, autologous), imitated biological materials, synthetic proteins such as collagen, biopolymers, polymers, synthetic textiles or solids. The substrate can also be a porous or spongy solid, such as an inorganic solid with a pumice structure. Such solids would be suitable for production of bone prostheses, among other things. The solid substrate could be developed in lumpy or tubular form. In general, the substrates can have any desired form, as long as they are suitable for circulation around them (internally and externally if desired) in inoculation The substrate can, if desired, by preserved by deep cold by introducing cold liquids or gases such as nitrogen in particular.

The objective of the invention is further attained by an inoculation device comprising a container and a holding means within it for a substrate to be inoculated. The holding means can be designed so that, in interaction with the substrate held within the container, at least two chambers which essentially separate liquids, or which allow controlled liquid transfer, are formed on opposites sides of the held substrate, and each of which also have a liquid inlet and outlet for each of the chambers formed.

The container of the inoculating device should be shaped so that the substrate is freely flushed by the culture medium when it is held in the holding means. The substrate can be held in any suitable way to the holder or holders. For instance, it can be tied, clamped, or sewed. The shapes of the container and holding means must be matched to each other. For example, the holder can comprise a vessel with a cover, having the cover connected to the holding means, with both together making up a removable insert.

A removable insert simplifies handling of the substrate before and after inoculating. When the insert is removed from the reactor, the substrate (that is, for instance, the finished implant) must not be touched or removed from the fixed parts of the reactor, which would be difficultly accessible in the interior of the reactor. This avoids a disadvantageous assembly/disassembly of the substrate being inoculated at fixed, non-removable parts of the housing. This substantially simplified both handling and use after transport to the final user under sterile conditions, such as in the surgery by the physician before implantation. The substrate removed from the reactor with the holding means is freely accessible, remains stabilized for the time being, and can, depending on the holding means, be removed very simply (untied, unclamped, cut loose). This substantially simplifies sterile manipulation of the finished inoculated substrate or implant.

The insert is designed so that the holding means lies at the inside of the container, so that there are two liquid-separating chambers formed on the sides opposite to the held substrate. Work is to be done with separate media or cells in the different chambers. Obviously, one can also work with the same cells and/or media on both sides of the substrate, inner and outer. A significant advantage of the apparatus is derived from the fact that cells (which may be different) can be flushed through repeatedly and that one can alternate between inoculation and perfusion phases without having to open the reactor. It may also be desirable to transfer fluid deliberately through the substrate, especially for organic substrates. The substrate to be inoculated supplements the insert so that one or more chamber dividing walls are formed. The holding means can also be designed to hold multiple substrates, with multiple chambers formed. Each of the chambers formed is preferably provided with liquid inlets and outlets. Likewise the substrate itself can already have multiple chambers, particularly double-walled or multi-walled with lumens between the walls. In this case, further development of the invention can provide that the holding means, preferably at one of the substrate holders, has at least one other inlet or outlet for adding medium, cells, and/or material in at least one internal chamber of this double-waled or multi-walled substrate.

If it is desired to produce a branched substrate, the holding means can be adapted appropriately, for instance, branched at one of the holders to produce a Y prosthesis.

Alternatively, the holder can be folded up or disassembled in a suitable manner so that the substrate held in the holding means can be placed in the inoculating device, and removed from it again, with minimal problem.

Preferably the holder of the inoculating device is itself designed so that it can be rolled or pivoted, so that during the entire inoculating time, or for certain inoculating steps, it can be inserted in a thermostated rolling incubator. For this purpose, the inoculating device can, for instance, be of cylindrical shape. This is particularly advantageous if a tubular substrate, such as a heart valve, or other tubular vessel, is to be inoculated. This embodiment is explained in more detail in the description of the figures.

In general, the holding means is preferably arranged essentially transverse to a preferred movement of a liquid medium in it, by a rolling or pivoting movement. The holding means can preferably be arranged, in relation to the inlets and outlets, so that a flow direction of the liquid medium determined by the inlets and outlets passes through the reactor along or within the held substrate.

For flat substrates, such as pieces of skin, the holding means can comprise at least one rack-shaped mount The rack-shaped mount would then preferably be mounted laterally to an insert piece which simultaneously forms a cover for a box-shaped holder. When the rack-shaped insert is inserted, the rack should touch the box-shaped container at three sides while the fourth side is connected to the lid fastened to the insert. This produces three chambers within the holder, each of which must be provided with inlets and outlets for liquid media. These inlet and outlet lines can be passed through the lid of the insert. As a box-shaped container is not itself rollable, it would be inserted into a mount for use in the rolling incubator. Such an arrangement is further described below.

The holding means can alternatively comprise two ring-shaped holders for the substrate, which are solidly connected together mechanically, as by rods.

The rollable or pivotable container can also be of spherical or spheroidal shape to allow more degrees of freedom of movement in the rolling incubator. Deflecting buttons can also be provided on the spherical container (or the spherical holder, see below) so that the direction of rolling is more frequently randomly changed during treatment in a rolling incubator or a corresponding apparatus, and so that rotation and pivoting are possible in all the spatial directions. The container can be made of a rigid or a flexible material. One of the advantages of the latter is that it allows variable volumes, to a certain extent, so that the substrate can expand more strongly, under pressure stress, for instance.

In addition to the liquid inlets and outlets through which the medium with the cells is passed in inoculation, the chambers can have one or more gas inlets and outlets. The gas inlets and outlets can have the form of tubes led along the walls and can consist of gas-permeable membranes such as silicone. Gases can be introduced through those to the culture medium, ore removed, during inoculation. Gas exchange can also be made possible, instead of or in addition to [the tubes] by gas-permeable outer walls of the container of the inoculating device.

For this purpose, the walls of the container can be made of PTFE or silicone film, or they may contain inserts of these structures or gas-permeable materials. The wall structures can be made of sintered metal, microporous ceramic, or porous glass. This porous carrier structure can be coated with a gas-permeable layer such as a plastic film (e. g., PTFE, silicone).

One advantage of the gas-permeable membranes or film integrated into the wall structures of the housing of the inoculating device is that the ambient atmosphere in the incubator (an ordinary rolling incubator or an apparatus made specially for this purpose) can be used directly for oxygen exchange and, with a carbon dioxide phase, also for pH regulation in the culture medium. It is important here that in this way the inoculation compartments (chambers) are simultaneously available as a culture reservoir and an oxygenation function for the inserted three-dimensional structure (such as a vessel or heart valve).

The inlets and outlets for the nutrient medium or the gas inlets and outlets can be connected to the inoculation device with rotary couplings, which make it possible for the inoculation to be carried out during rolling of the inoculation device in a rolling incubator specially designed for the purpose. The lines connected through the coupling could be made concentric for this purpose.

Finally, it is possible in a further development of the invention that certain inserts are arranged within the container to direct the liquid medium in a desired manner as it flows through the reactor. These can be rods or tubes arranged on the inner wall of the container. suitable inserts in the broader sense are known from reactor design for other purposes.

The reactor container can also be provided with or connected to means, themselves known, for heating or cooling. For instance, heating wires for tempering the medium can be inserted into the outer wall of the reactor. The reactor holder can also be jacketed for a heating or cooling medium such as water.

The culture medium is passed from the inlets and outlets through the reactor, which in one embodiment contains the cells being inoculated. Alternatively a certain quantity of cells can be placed in the reactor, in which case only the pure culture medium circulates. The inlets and outlets are preferably provided with filters to prevent undesired removal of cells. In addition, the inlets are outlets are provided with seals (cutoff valves) so that the individual chambers can be closed. The recirculation of cells is preferably avoided by the process of the invention. In contrast to the previous flow inoculation, in this case the cells are maintained above the substrate.

As already pointed out above, there is a holding means in the interior of the container for the substrate to be inoculated. The substrate is held in a holding device during the inoculation so that it is freely accessible on the desired sides for the culture medium and the cells and does not fold up or stick together. At the same time, the holder acts to introduce the substrate into the reactor by means of the preferably removable insert, and to remove it again. The removable insert thus serves at the same time for improved handling of the substrate, which is inserted into it, for instance, immediately after inoculation in a liquid, and can be handled or preserved in other ways.

As the substrate being inoculated must stick continuously to the surface between the inlet and outlet within the holding means, it is also possible to use intermediate segments of, for instance, fiber-reinforced tubes or silicone funnels or other, preferably elastic, plastics to adapt the length and size. These can be movable to cover distances or for shortenings.

According to the invention the holding means is essentially transverse to a preferred direction of movement established by the rolling or pivoting motion of the holder or the holder mounted in the mount described below. "Essentially transverse" is intended to mean that the moving liquid medium, i. e., the cell suspension in the culture medium, is "thrown onto" the substrate continuously at an angle between 30° and 150° to the axis of rotation of the rolling or pivoting movement. That is, it is repeatedly brought into contact with it Here the preferred direction of movement of the liquid medium is considered, neglecting a simultaneous, if possible (but not essential) flow of the liquid medium along the held substrate.

In the inoculation, i. e., during at least certain periods of inoculation, the rollable or pivotable container, i. e., the inoculation device as a whole, is placed in a rolling incubator or an apparatus for pivoting, or a comparable device with corresponding function, where it is rolled or pivoted to move the culture medium and the cells suspended in it relative to the held substrate.

The inoculating device is treated just like a roll flask in the rolling incubator. That is, it is rolled and, if desired, temperature-controlled. In place of the rolling incubator, however, any other device can be used that is suitable for moving the inoculating device in the desired manner. That can also be a separate apparatus provided specially for this purpose. The rolling incubator or the apparatus can also provide a specific atmosphere (oxygen, carbon dioxide).

The passage of culture medium or cell suspension through the reactor by means of the liquid inlet and outlet, or by means of multiple inlets and outlets, need not continue through the entire inoculation process. It can also be particularly convenient to stop the flow for a time, for example, during rolling in the rolling incubator or during treatment in a device for the corresponding purpose. That can be done by temporarily clamping off the inlets and outlets, or by closing them with valves.

The culture medium, with or without cells, can be recirculated at least temporarily through the inlets and outlets. In this way, cells which could not attach in the first pass are again offered to the substrate.

The movable cells in the culture medium which have not yet attached [to the substrate] are carried to the substrate through the inlet, and then distributed along the substrate. The distribution "transverse" to this longitudinal direction is done essentially by the rolling or pivoting motion. Both motions can be superimposed, and then cooperate. The rolling or pivoting movement can be superimposed with other types of motion, such as vibratory motion, for the purpose of bringing the cells repeatedly back into contact with the substrate and distributing them on it.

The fact that a flow can be established along the substrate makes possible an evenly distributed provision of cells to all points of the substrate. The flow velocity can be set so that the transport of the cells does not, as much as possible, prevent ingrowth of the cells. The ingrowth can also be promoted by stopping the flow of culture medium temporarily so that the cells immediately above the substrate remain there for a time and have the opportunity for attachment and ingrowth.

The invention further comprises an arrangement of an inoculation device as described above and a holder designed to be rollable. The holder is used so that holders which are not rollable as such, e. g., a box-like holder, can be handled in a rolling incubator, or to introduce additional directions of motion. Preferably, the axis of rotation of the roll e holder and a longitudinal axis of the substrate held in the holding device of the inoculating device are at an angle to each other.

A rotationally symmetric body having one or more recesses or sockets for an inoculating device as described above can be used as a holder for the arrangement cited above. This rotationally symmetric body can be made of a suitable material such as glass, plastic or metal. For instance, the holder can comprise a sphere with a tubular passage. Then a cylindrical reaction container can be inserted into this tubular passage. (There may be multiple tubes for multiple containers). Then the sphere can be placed in a rolling incubator after clamping off the inlet and outlet lines of the inoculating device, so that the substrate is turned in all directions during the rolling. The holder can comprise a cylindrical body or frame in which a tubular passage is placed obliquely to the cylinder axis. On rolling of the inoculating device in this holder, the holder and, thus, the substrate, are subjected to an additional turning motion transverse to their longitudinal axis.

After inoculation of the substrate, the inoculating device is also suitable to act as a transport and storage container for the already populated substrate. That avoids further direct handling of the sensitive populated substrate. For instance, it need not be removed from the culture solution. Rather, it can remain in the inoculating device until it is used. The inlets and outlets, and the gas inlet and outlines, can be clamped for transportation. Otherwise, it is possible to leave the inoculated substrate in the desired medium (continuously renewable) under any desired atmosphere.

The substrate can also be cooled in the inoculating device. Cryogenic preservation of an inoculated or an uninoculated substrate can be achieved by introducing cooling liquids or gases (such as nitrogen) into at least one chamber, or, better, all chambers at once. Cryogenic preservation can also be done for storage before inoculation of the substrate. That can, for instance, be linked with a sterilization phase.

In a further embodiment of the invention, an additional chamber with at least one inlet and outlet can be formed at the inner wall of the container of the inoculating device using a microporous dividing wall. Multiple chambers can also be produced in the same manner. Separate media or cultures ("feeder cultures") which provide one or more inoculation chambers in the device with specific nutrients or factors can be maintained [see Note 3] in these chambers.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
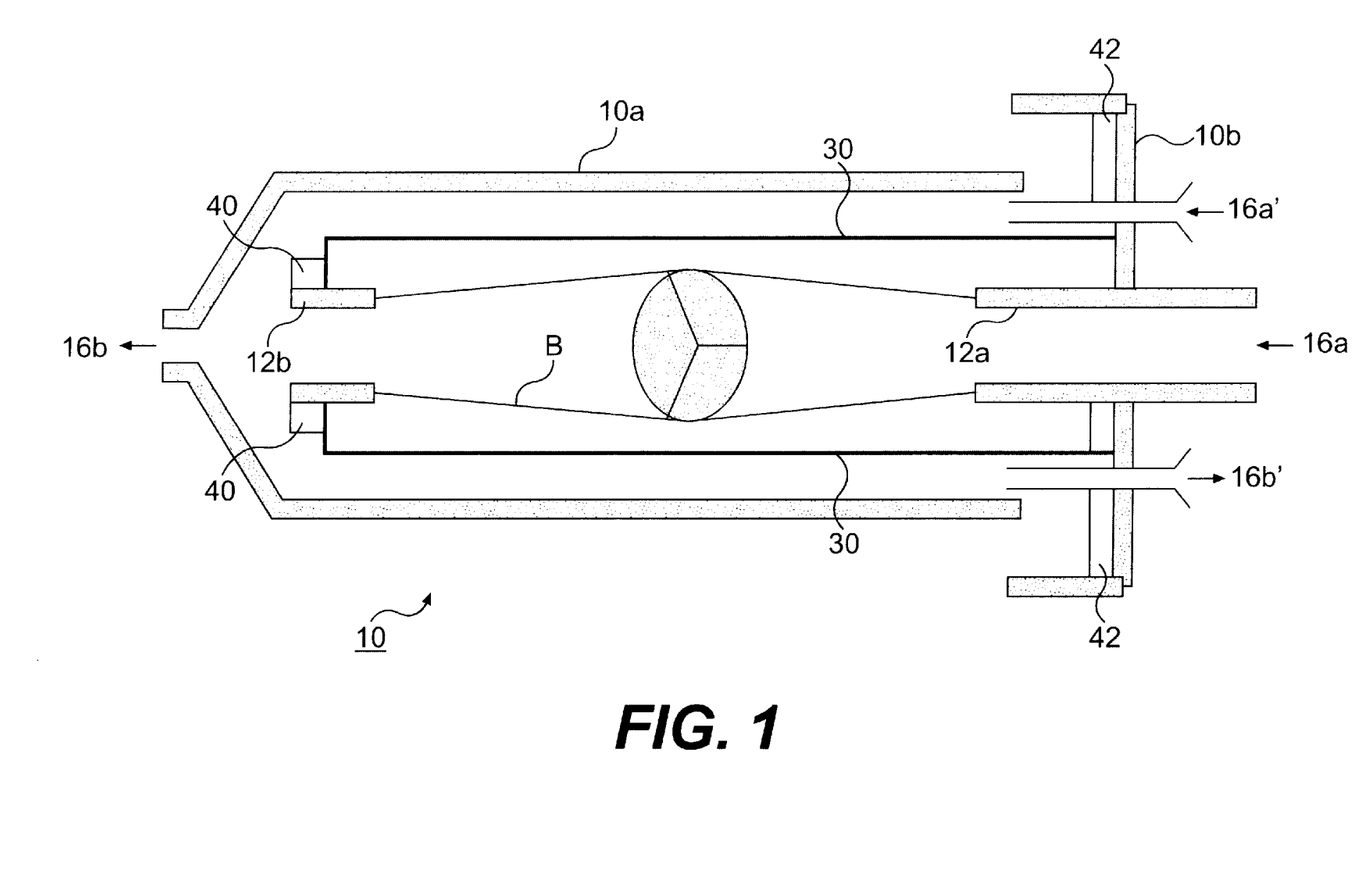
FIG. 1 shows a cylindrical two-chamber inoculating device for a tubular substrate, in a longitudinal section in an exploded presentation.

FIG. 1 shows a first example embodiment of the invention in a longitudinal section in an exploded presentation. This is a cylindrical inoculating device designed for inoculating a tubular substrate, designated by B in the drawing. The holder 10 comprises two holder parts 10a, 10b, which are not plugged together in the drawing. The liquid inlet 16a also forms, on the inside, of the device, a first ring-shaped or tubular holder 12a for the substrate. The second ring-shaped holder 12b is connected by rods 30 to the container cover 10b, so that it is firmly connected mechanically to the first holder 12a. The holders 12a and 12b together make up the holding device for the tubular substrate B, a heart valve. When the holder parts 10a and 10b are pushed together, the holder 12b seals against the inner wall of holder part 10a with the sealing ring 40 and the outlet 16b is sealed off. At the same time, the holder 10, made of the holder parts 10a and 10b, is closed and sealed with the seal 42. This, with the clamped substrate B, forms two chambers, one in the inside of the tubular substrate B, and one around the outside of the substrate. The cell suspension and/or the culture medium is introduced through the inlet 16a to provide cells to the interior of the substrate. It runs in through the ring-shaped holders 12a and 12b and the substrate and is removed again through the outlet 16b. The inlet 16a and outlet 16b are kept closed during the inoculation phase. After completion of the inoculation phase, the medium is removed again through outlet 16b. The cell suspension and/or culture medium for inoculating the outer surface of the substrate is added through inlet 16a', is distributed around the substrate B in the interior of the container, and is removed again through outlet 16b'. The inoculation is otherwise done as previously described.

During the perfusion phase, the two separate chambers or compartments can be perfused separately. The perfusion can be done with various growth factors and concentrations, so that different media specific for the cell type can be provided and internal gradients can be produced. Inoculation and perfusion phases can alternate without it being necessary to open the reactor.

At the end of the treatment the insert with the substrate can be removed completely by removing the lid, like a drawer. Handling of the finished substrate, such as a heart valve implant in this case, is substantially simplified by that, and reliability of sterility and integrity of the substrate is increased.

Figure 2:
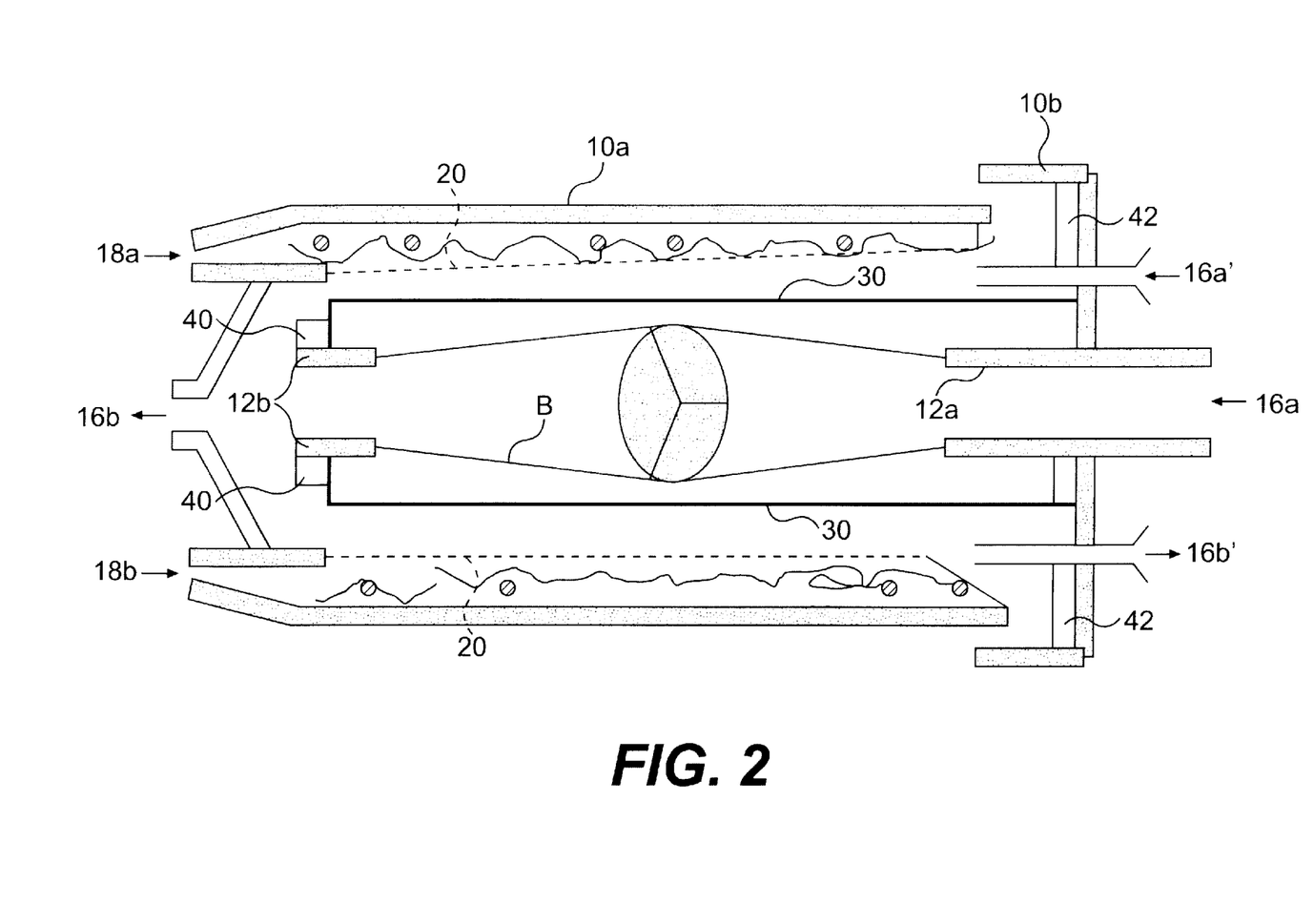
FIG. 2 shows a device such as is presented in FIG. 1, with an additional chamber at the inner side of the container formed by a porous dividing wall.

FIG. 2 shows a device as in FIG. 1, in which an additional chamber is divided off by a microporous dividing wall 20 at the inner wall of the cylindrical container 10a, that is, inside the cylindrical jacket. This additional chamber can be provided with the desired medium through at least one inlet 18a and at least one outlet 18b. Exchange between the additional chamber and the interior of the container is provided by the microporous dividing wall. For this purpose, nutrients or certain gases can be generated within the added chamber. They can then be provided to the substrate through communication with the interior of the holder. The microporous dividing wall can, for instance, be made of a silicon film, PTFE, sintered glass, polycarbonate, cellulose, polyamides, or other plastics.

Figure 3:
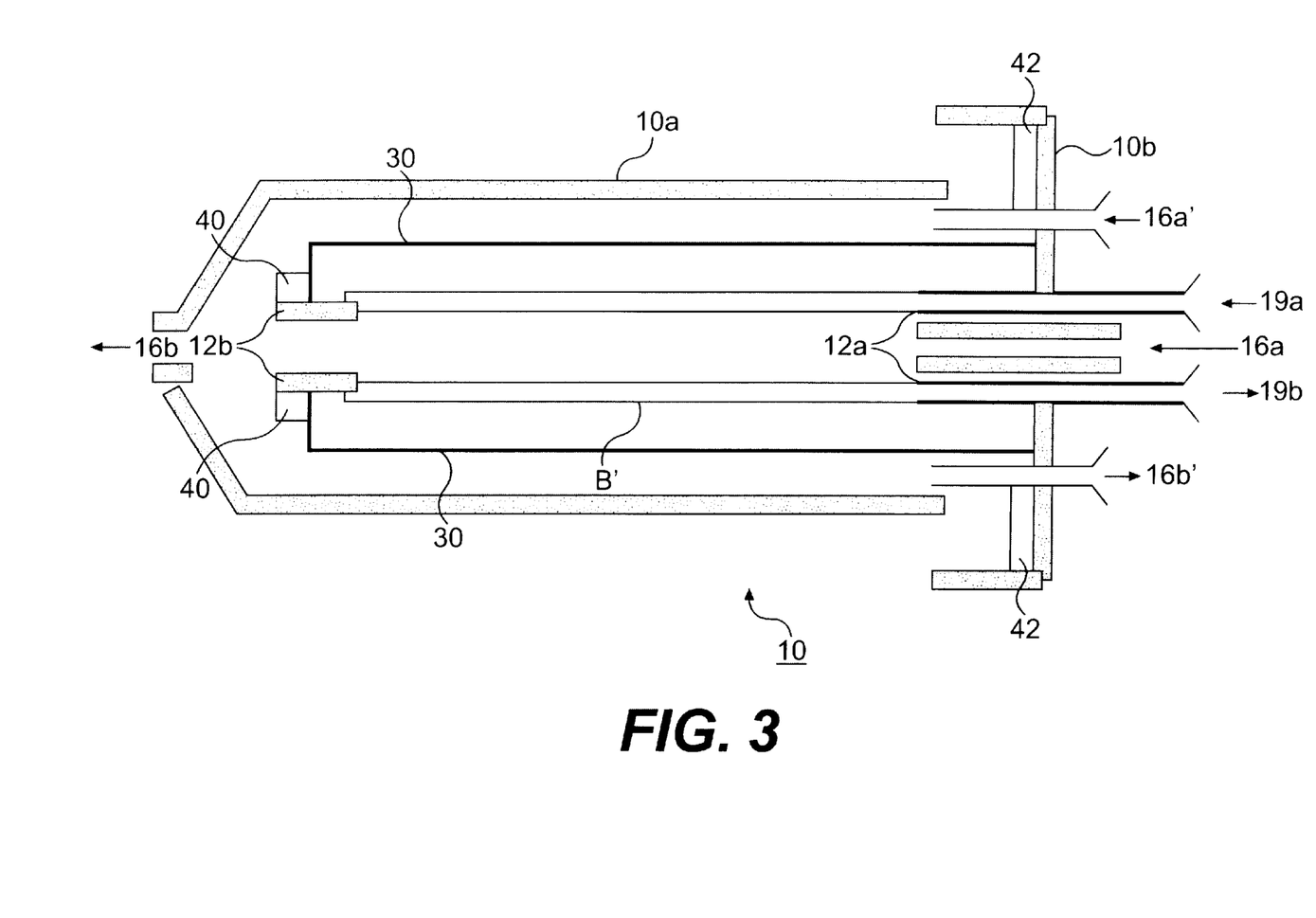
FIG. 3 shows a cylindrical two-chamber inoculating device for a double-wall tubular substrate, in a presentation corresponding to that of FIG. 1.

FIG. 3 shows a cylindrical two-chamber inoculating device 10 for a double-walled tubular substrate B'. The inoculating reactor is very similar to the example shown in FIG. 1, and identical reference numbers indicate identical parts. The difference from the inoculating device of FIG. 1 is that this reactor is suitable for an at least double-walled substrate and has two additional inlets and outlets 19a, 19b, by means of which medium or material can be introduced into a lumen between the walls of the double-walled substrate B'. These inlets/outlets 19a/19b are placed on the single holder 12a of the holding device. The holders 12a and 12b hold the tubular, but double-walled, substrate at both ends, with the ends of the substrate combined or bound together at the holder 12b, while the inlet and outlet, 19a, 19b, are introduced between the two walls of the substrate at holder 12a. Then the interior of the substrate can be supplied with the desired medium or material, or with more cells.

Figure 4:
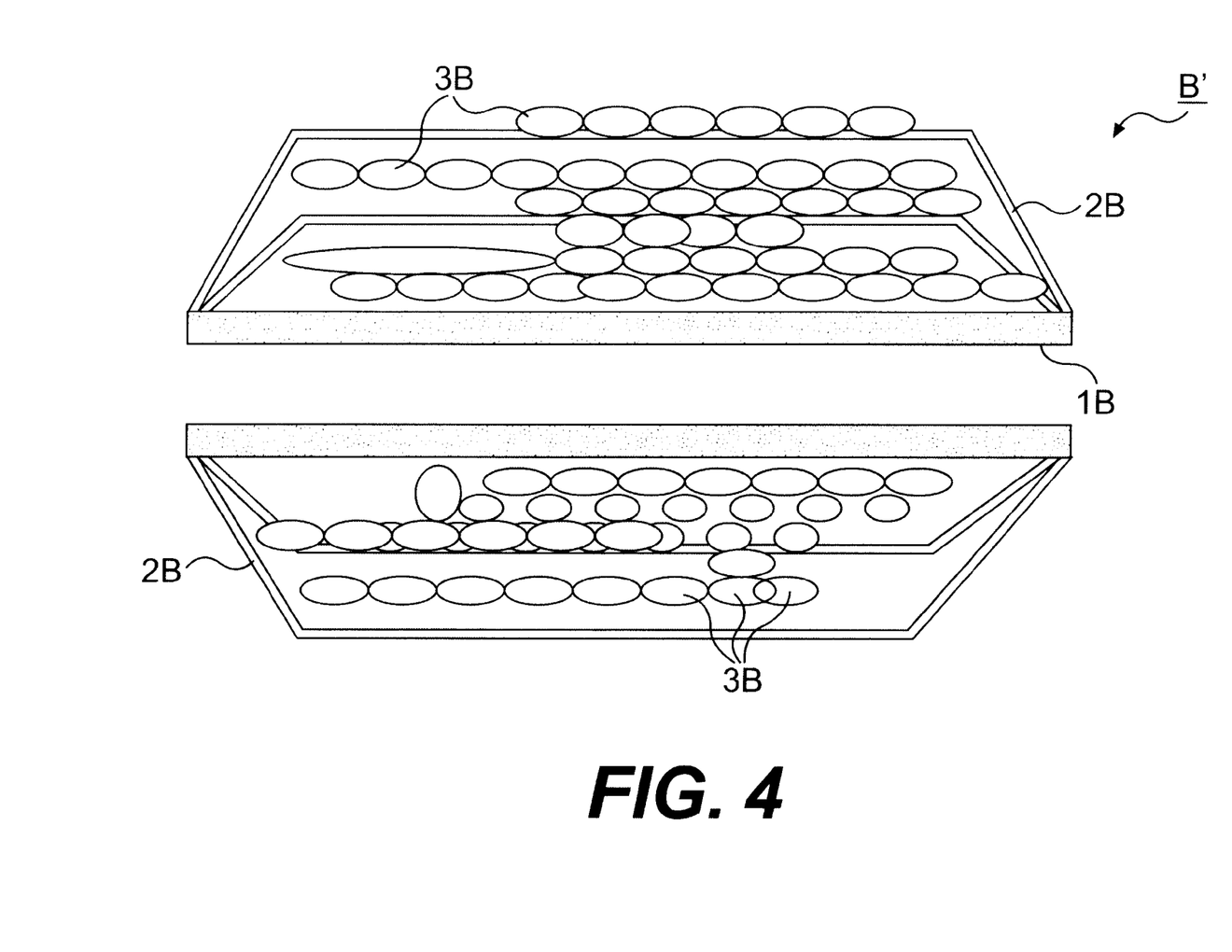
FIG. 4 shows a multi-wall substrate in longitudinal section (without the reactor).

FIG. 4 shows another example embodiment of such a multi-walled substrate B'. In this case the substrate is triple-walled. Here the substrate can preferably be a synthetic substrate. In this example, the inner wall of this substrate is designated as 1B. Furthermore, there are two other shells 2b, which hold any desired materials or cells in layers on the inner substrate. Here the substrate is combined at its ends, so that it mounted jointly on the holders 12a, 12b, not shown.

Communication with the nutrient or inoculating medium is not as shown in FIG. 3, through the inlets and outlets 19a, 19b, but by diffuision transverse to the direction of flow. In this example, cells 3B are shown, which are applied in and on the substrate. The multilayer substrate structure allows distinctly thicker substrates, so that, for instance, tissues can be developed with capillarity as in nature under the local differentiation pressure.

In another example embodiment, the substrate could comprise a solid material, especially a solid inorganic material. For instance, a calcium-containing solid material, particularly a solid material containing tricalcium phosphate, such as a possibly sintered or cemented compressed granulation could be used as the inorganic solid material. Material can be implanted very well in the porous wall structure of the solid with such a porous solid material, using the bioreactor according to the invention.

In each case, the bioreactor technology has the great advantage that the products intended as implants are only removed from the reactor in the surgery immediately before implantation, so that a closed sterile operation is assured from the initial handling of the substrate up to implantation of the populated substrate in a patient.

Tubular bone implants can be produced particularly advantageously in the bioreactor according to the invention, as the interior of the tube can be inoculated separately from the exterior of the tube.

Figure 5:
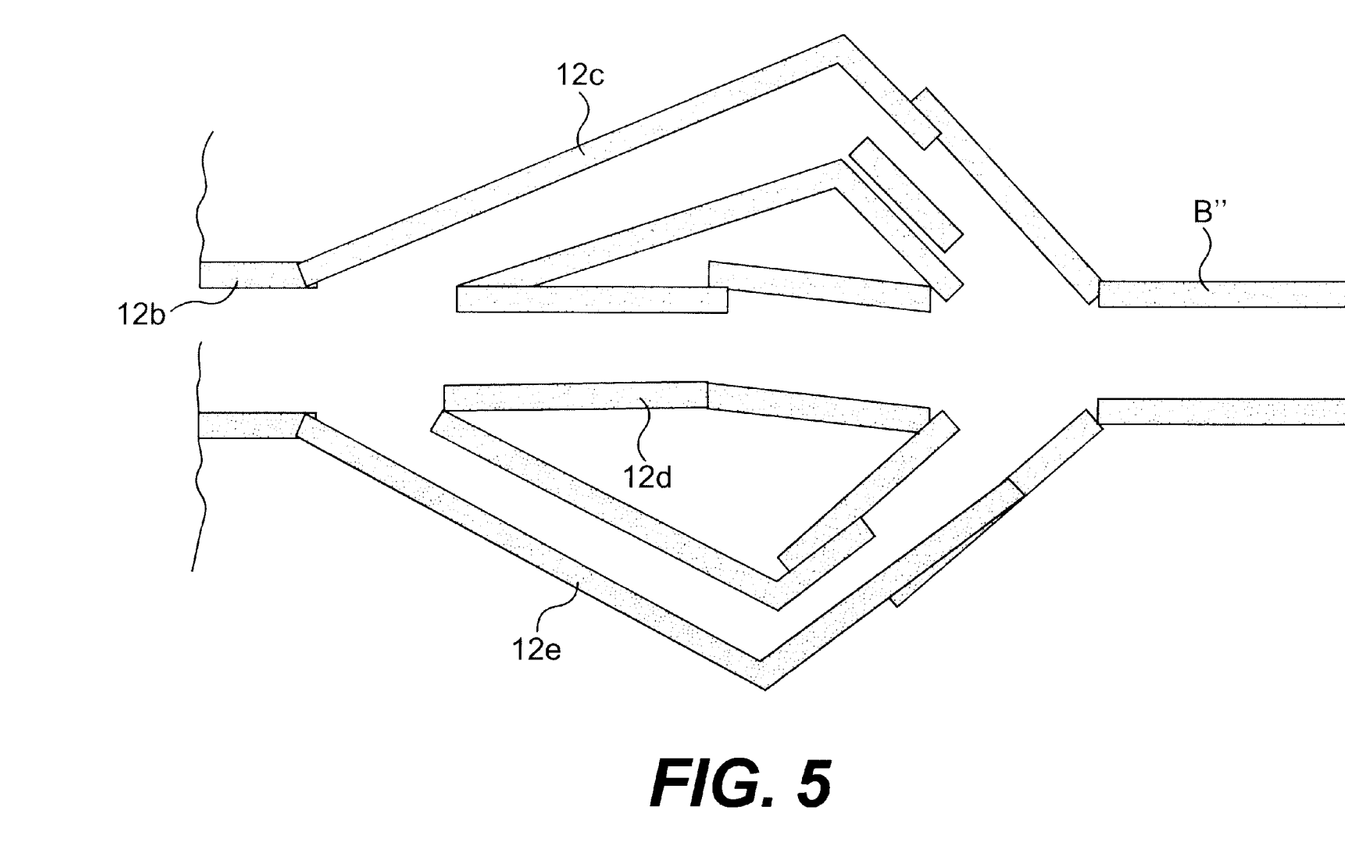
FIG. 5 shows a partial view of a holding device for a branched substrate (also shown in partial view).

FIG. 5 shows a partial view of a holding device for a branched substrate, which is itself also shown in a partial view. The holder 12b of the holding device branches in this case into the tubular holder sections 12c, 12d, and 12e, each developed as a branch of the Y prosthesis B", in this case, with the device such as is shown in FIGS. 1 to 3.

Figure 6:
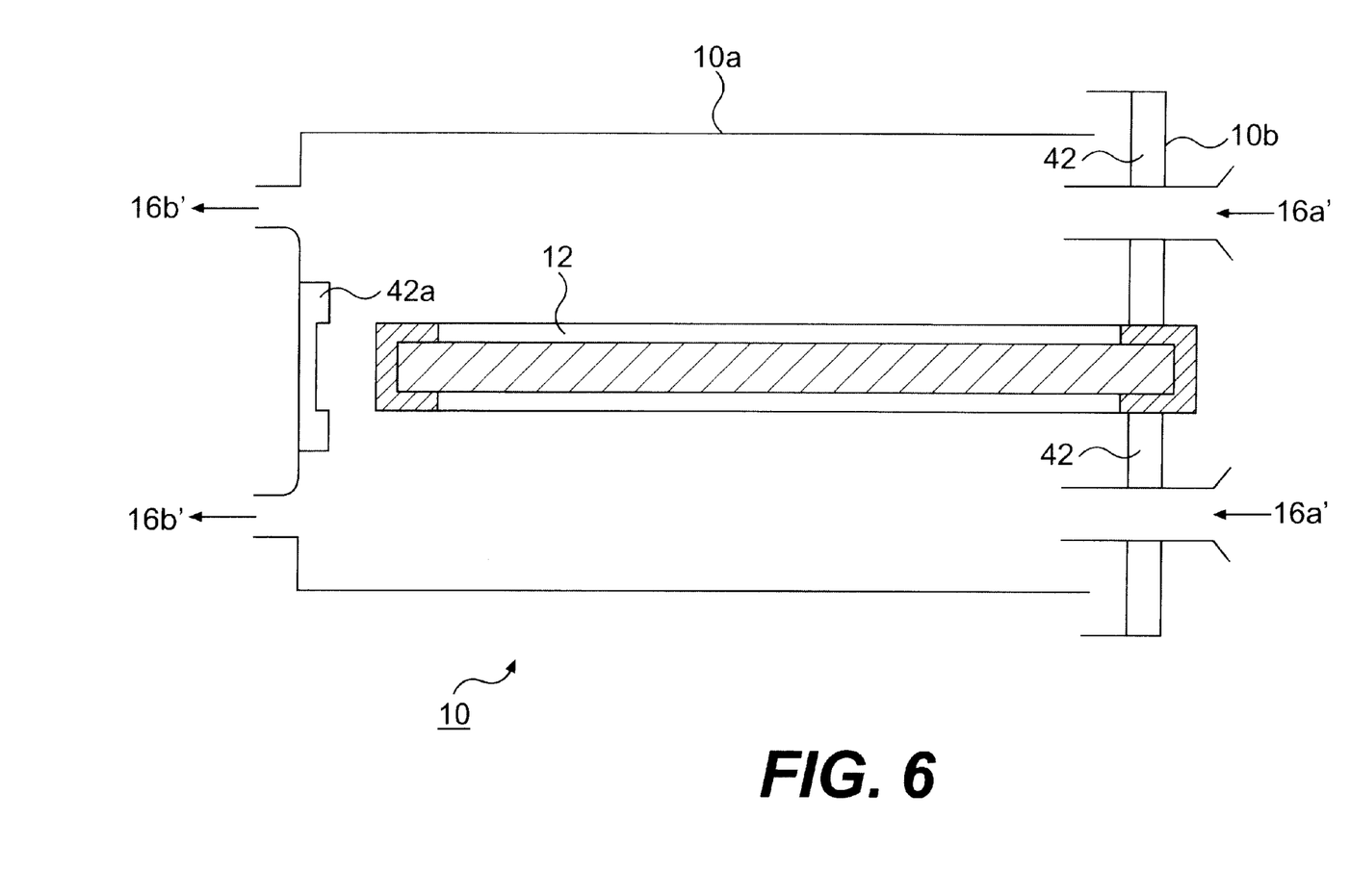
FIG. 6 shows a cross-section through a box-shaped inoculating device with a frame-like holding device.

FIG. 6 shows another example embodiment of an inoculating device having a box-shaped container 10a with a rectangular lid 10b. Inside this container 10 there is a frame-like holding device 12, which is firmly connected to the lid 10b. The insert, made up of the holding device and lid, is sealed against the container 10a by means of the seals 42. Seal 42a is a U-shaped seal surrounding the frame-like holding device 12 in the interior of the container, which can be shown in a suitable manner in profile. In the assembled state, two liquid-separating closed chambers are formed inside the inoculating device, one above and one below the substrate.

Internal fluid transfer between the chambers may be desirable and possible, depending on the porosity of the substrate being inoculated. In this way, it is possible for oxygenated medium to get also into the inner structure during the rolling phase of the inoculating device.

Each of the chambers has a liquid inlet 16a, 16a' and a liquid outlet 16b, 16b'. Gas inlets and outlets can also be provided, but are not shown here. As long as the reactor is rolled during the inoculation, the inlet and outlet lines 16a, 16a', 16b, 16b' are clamped off. If that is not desired, rotating couplings are provided. Usually, though, the process is done in steps.

Figure 7:
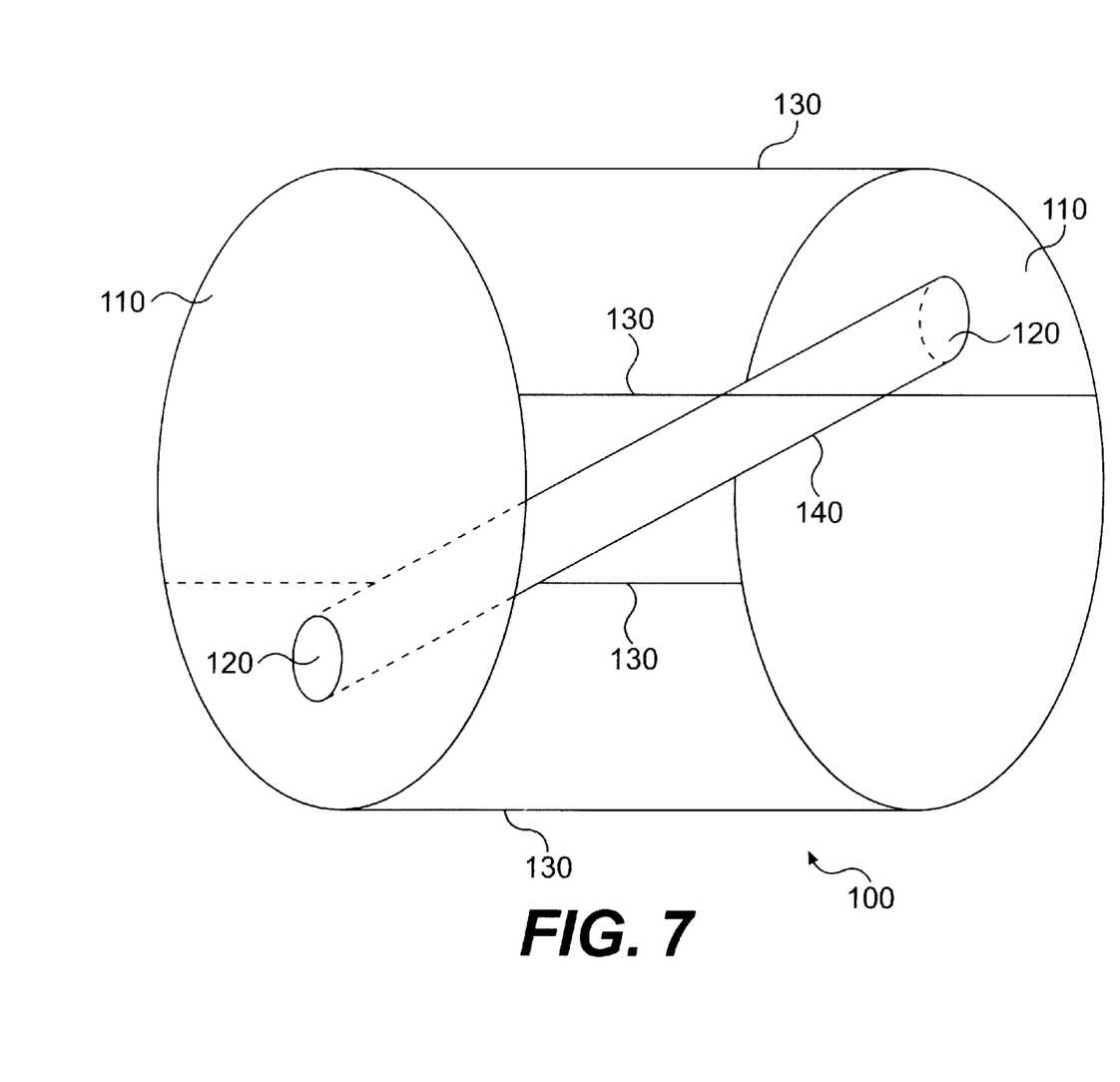
FIG. 7 shows a holder for a cylindrical inoculating device according 5 to the invention.

FIG. 7 shows a suitable rollable holder 100 in which the inoculating device 10 can also be turned in a rolling incubator during the inoculation. The holder 100 comprises two disks 110 of glass or Plexiglas with two eccentric openings 120. The openings 120 for insertion of a cylindrical inoculating device 10 are best oval or in the shape of a section of a cylinder. In this example the disks 110 are circular, but they can have other shapes; for instance, they can be elliptical. In this example the disks 110 are connected by multiple rods 130. However, they can also be connected by a closed cylindrical jacket. The mounting of the disks 110 is chosen so that the openings 120 are oppositely displaced in the projection. A tube 140 is inserted between the openings 120, into which the inoculating device 10 can be inserted. Then the longitudinal axis of the inoculating device, not shown in the drawing, is oblique to the longitudinal axis of the overall cylindrical holder. The holder 100, with the inoculating device 10 makes up an arrangement which can be placed in a rolling incubator. On treatment in the rolling incubator, the inoculating device is exposed to a rolling movement about its long axis and simultaneously a turning movement transverse to its long axis. In this way the culture medium can be distributed and brought into contact with the substrate particularly intensively and evenly.

The sidewalls of the devices shown in the figure (outer walls in the shape of a cylindrical jacket, rectangular, or spherical) can, for example, consist of gas-permeable PTFE or silicone films to improve the oxygen supply during perfusion-free inoculation phases. Continuous gas exchange, or deliberate temporary oxygenation with oxygen or an oxygen mixture substantially increases the adhesion efficiency (up to 100–200%) during the rolling phase. In this way the substrate is optimally supplied with oxygen at all times (rolling phase and perfusion phase). Because of the rolling, used medium moves continuously to the oxygenating reactor wall.

Having thus described our invention, what we claim as new and desire to secure by Letters Patent is as follows:

1. A process for inoculating substrates with biological cells comprising the steps of:
    holding a substrate within a inoculating device such that the substrate divides the inoculating device into at least two chambers, wherein each of said at least two chambers accesses different surfaces of the substrate;
    subjecting at least one of said at least two chambers to an at least one inoculation phase, during which the substrate can be rotated about at least one axis, and the cells are brought repeatedly into contact with the substrate during the rotary motion; and
    subjecting said at least one of said at least two chambers to an at least one perfusion phase.

2. The process according to claim 1 wherein during said inoculation phase, cells are transported onto the substrate by a method selected from the group consisting of transporting the cells onto the substrate in a medium, streaking the cells on the substrate, moving the cells into the substrate, and coating the substrate with a paste containing the cells.

3. The process according to claim 2 wherein one or more additives selected from the group consisting of factors, cofactors, growth factors, and chemotactic factors are added to the cells.

4. The process according to claim 1 wherein during said perfusion phase, the substrate is perfused with a liquid medium selected from the group consisting of a cell culture nutrient medium and blood.

5. The process according to claim 1 wherein said rotation is done about at least two spatial axes at the same time in a superimposed rotary movement.

6. The process according to claim 1 wherein said rotation is performed about at least two spatial axes in succession.

7. The process according to claim 1 wherein said inoculation and perfusion phases are carried out alternately.

8. The process according to claim 1 further comprising the step of a resting phase after said at least one inoculation phase, wherein during said resting phase, there is no rotation and no perfusion.

9. The process according to claim 1 wherein the process comprises other phases with additional process steps for treatment of the substrate.

10. The process according to claim 1 wherein the perfusion phase is done with pulsation.

11. The process according to claims 1 wherein the different surfaces of the substrate are inoculated with different cell types.

12. The process according to claim 1 wherein the substrate is inoculated with different cell types in succession or at different positions on the substrate.

13. The process according to claim 1 tinier comprising the step of an additional treatment of the substrate wherein one or more of the additional treatments is selected from the group consisting of having the substrate acellularized, sterilized, transported, and stored in the inoculation device.

14. The process according to claim 1 further comprising the step of temporarily preserving the substrate by deep freezing wherein the step of freezing is done by introducing cooling liquid or gases to the substrate.

15. An inoculating device comprising:

a holder;

a holder device within the holder for holding a substrate to be inoculated, wherein when the substrate is positioned in the holder device, the substrate divides the holder into at least two chambers wherein each of said at least two chambers exposes different surfaces of the substrate; and at least one inlet and outlet for each of said at least two chambers.

16. The inoculating device according to claim 15 wherein the holding device is in a removable insert so that the substrate with the holding device can be removably inserted into the holder.

17. The inoculating device according to claim 15 wherein the holder has a rotationally symmetric body.

18. The inoculating device according to claim 15 further comprising one or more holding devices arranged essentially transverse to a direction of flow of a liquid medium in the holder when the holder is rolled.

19. The inoculating device according to claim 15 wherein the holding device is arranged in relation to the inlets and outlets such that a flow of liquid medium established by said inlets and outlets runs through the holder along the mounted substrate.

20. The inoculating device according to claim 15 wherein the holding device comprises at least one frame-like holder.

21. The inoculating device according to claim 15 wherein the holding device has at least one branched holder for holding a Y prosthesis.

22. The inoculating device according to claim 15 wherein the holding device has at least one other inlet and outlet for each chamber formed from a multi-walled substrate.

23. The inoculating device according to claim 15 wherein the holder is cylindrical.

24. The inoculating device according to claim 15 wherein the holder is spherical.

25. The inoculating device according to claim 15 wherein at least one of said at least two chambers includes one or more gas inlet and outlet lines.

26. The inoculating device according to claim 15 wherein said at least one inlet and outlet are connected to the holding device through rotary couplings.

27. The inoculating device according to claim 15 wherein said holder is made of gas-permeable walls.

28. The inoculating device according to claim 15 further comprising inserts on the inner wall of the holder such that the inserts direct liquid medium while it is flowing through the holder.

29. The inoculating device according to claim 15 having an additional chamber with at least one inlet and outlet, wherein said additional chamber is formed at an interior wall of the holder by a microporous dividing wall.

30. The inoculating device according to claim 15 wherein the axis of rotation of the holder and a longitudinal axis of the substrate held in the holding device are at an angle to each other.

* * * * *